(12) United States Patent
Honda et al.

(10) Patent No.: US 10,921,260 B2
(45) Date of Patent: Feb. 16, 2021

(54) OPTICAL MEASURING DEVICE

(71) Applicants: HAMAMATSU PHOTONICS K.K., Hamamatsu (JP); SEKISUI MEDICAL CO., LTD., Tokyo (JP)

(72) Inventors: Naoyuki Honda, Hamamatsu (JP); Kengo Sadamori, Hamamatsu (JP); Daichi Susuki, Hamamatsu (JP); Keigo Kohno, Tokyo (JP); Motoki Morita, Tokyo (JP)

(73) Assignees: HAMAMATSU PHOTONICS K.K., Hamamatsu (JP); SEKISUI MEDICAL CO., LTD., Tokyo (JP)

( * ) Notice: Subject to any disclaimer, the term of this patent is extended or adjusted under 35 U.S.C. 154(b) by 219 days.

(21) Appl. No.: 15/766,544

(22) PCT Filed: Oct. 5, 2016

(86) PCT No.: PCT/JP2016/079672
§ 371 (c)(1),
(2) Date: Apr. 6, 2018

(87) PCT Pub. No.: WO2017/061494
PCT Pub. Date: Apr. 13, 2017

(65) Prior Publication Data
US 2018/0299385 A1    Oct. 18, 2018

(30) Foreign Application Priority Data

Oct. 9, 2015  (JP) .................................. 2015-200977

(51) Int. Cl.
*G01N 21/78*    (2006.01)
*G01N 33/543*   (2006.01)
*G01N 33/58*    (2006.01)

(52) U.S. Cl.
CPC ....... *G01N 21/78* (2013.01); *G01N 33/54366* (2013.01); *G01N 33/583* (2013.01)

(58) Field of Classification Search
CPC ............ G01N 21/78; G01N 33/54366; G01N 33/583; G01N 33/543
See application file for complete search history.

(56) References Cited

U.S. PATENT DOCUMENTS

| 7,173,704 B2 | 2/2007 | Yamauchi |
| 7,239,394 B2 | 7/2007 | Sharrock et al. |

(Continued)

FOREIGN PATENT DOCUMENTS

| CN | 101650298 A | 2/2010 |
| CN | 101821624 | 9/2010 |

(Continued)

OTHER PUBLICATIONS

International Preliminary Report on Patentability dated Apr. 19, 2018 for PCT/JP2016/079672.

*Primary Examiner* — Dennis White
(74) *Attorney, Agent, or Firm* — Faegre Drinker Biddle & Reath LLP

(57) ABSTRACT

An optical measuring device includes a measuring unit (an optical head and a control unit) that irradiates a detection portion of an immunochromatographic test piece with measurement light and measures light obtained from the detection portion due to the irradiation with the measurement light, and a determination unit that performs a determination regarding the immunochromatographic test piece on the basis of a determination according to a comparison of a measurement value obtained by the measuring unit with a preset threshold value, the measuring unit performs the measurement of the light obtained from the detection portion a plurality of times, and the determination unit performs a determination regarding the immunochromatographic test (Continued)

piece when the determination unit determines that a measurement value in an nth measurement is equal to or greater than the threshold value and also determines that a measurement value in an (n+1)th measurement is equal to or greater than the threshold value.

8 Claims, 9 Drawing Sheets

(56) References Cited

U.S. PATENT DOCUMENTS

| | | | |
|---|---|---|---|
| 7,315,378 B2 | 1/2008 | Phelan et al. | |
| 7,317,532 B2 | 1/2008 | Sharrock et al. | |
| 7,616,315 B2 | 11/2009 | Sharrock et al. | |
| 8,133,742 B2 | 3/2012 | Yamauchi | |
| 9,470,678 B2 | 10/2016 | Ding et al. | |
| 9,933,362 B2 | 4/2018 | Sharrock et al. | |
| 2005/0036148 A1* | 2/2005 | Phelan | G01N 21/4738 356/446 |
| 2005/0036915 A1 | 2/2005 | Yamauchi | |
| 2010/0087010 A1 | 4/2010 | Yamauchi | |

FOREIGN PATENT DOCUMENTS

| | | |
|---|---|---|
| EP | 1688743 A1 | 8/2006 |
| EP | 1484601 B1 | 2/2009 |
| EP | 1484611 B1 | 12/2015 |
| EP | 2293068 B1 | 1/2017 |
| EP | 2811301 B1 | 5/2017 |
| EP | 2282204 B1 | 11/2017 |
| JP | 2005-134211 A | 5/2005 |
| JP | 2007-40939 A | 2/2007 |
| JP | 2008-170187 A | 7/2008 |
| JP | 2009-133813 A | 6/2009 |
| JP | 4630003 B2 | 2/2011 |
| JP | 2011-174865 A | 9/2011 |
| JP | 4812264 B2 | 11/2011 |
| JP | 5079972 82 | 11/2012 |
| JP | 5378463 B2 | 12/2013 |
| JP | 6359263 B2 | 7/2018 |
| WO | WO-02/052265 A1 | 7/2002 |
| WO | WO 2004/077030 A1 | 9/2004 |
| WO | WO-2010/058472 A1 | 5/2010 |

\* cited by examiner

OPTICAL MEASURING DEVICE

TECHNICAL FIELD

The present invention relates to an optical measuring device that is used for detection of an antigen or antibody using an immunochromatography method.

BACKGROUND ART

An immunochromatography method is a detection method for detecting an antigen (or antibody) in a specimen using a test piece to which a reagent that contains an antibody (or an antigen) causing an antigen or antibody reaction is applied to a measurement position thereon. When the antigen (or antibody) in a specimen labeled with a pigment develops to the detection position, an antigen (or antibody) in the specimen causes the antigen and antibody reaction with the antibody (or antigen) applied in a band shape and is trapped, and a coloration line colored by the pigment develops on a test line. Therefore, it is possible to quantitatively analyze the antigen (or antibody) in the specimen by optically measuring a degree of coloration of the coloration line in the test piece using an optical measuring device.

Examples of an optical measuring device that is used in the immunochromatography method include optical measuring devices described in Patent Literature 1 and 2. The optical measuring devices include a loading unit onto which a plurality of test pieces are loaded, a reading unit that reads a coloration state of the test piece loaded onto the loading unit, and a control unit that performs an inspection process on the basis of the coloration state of the test piece read by the reading unit. Although a reaction completion time has been set for a reagent that is used for the test piece in advance, the control unit uses a degree of coloration of a coloration line read in a period from loading of the test piece onto the loading unit to reaching of the reaction completion time to determine completion of the test.

CITATION LIST

Patent Literature

[Patent Literature 1] Japanese Unexamined Patent Publication No. 2009-133813
[Patent Literature 2] International Publication WO 2010/58472

SUMMARY OF INVENTION

Technical Problem

Performing various determinations before the reaction completion time set for each reagent has been reached as in the optical measuring device of the related art described above contributes to an improvement in throughput of the device, and is considered to be very useful also when the number of inspection targets is large. However, when the determination is performed before the reaction completion time has been reached, a guarantee of accuracy of the determination is an important issue.

Generally, a reaction of a reagent in an immunochromatography method progresses over time after a specimen is dropped onto a test piece. The reaction of the reagent normally continues to progress as long as the specimen dries and does not stick to the test piece, and the degree of coloration of the test line varies with time. Further, when the specimen develops, the pigment or the like may flow in a lump, and a great temporary fluctuation in the degree of coloration of the test line is conceivable. When a determination is performed by disregarding such a fluctuation in the degree of coloration, there is concern that an erroneous determination may be caused.

The present invention has been made to solve the above-described problems, and an object of the present invention is to provide an optical measuring device capable of rapidly and accurately performing determination on an immunochromatographic test piece.

Solution to Problem

In order to solve the above problem, an optical measuring device according to an aspect of the present invention includes a measuring unit that irradiates a detection portion of an immunochromatographic test piece with measurement light and measures light obtained from the detection portion due to the irradiation with the measurement light; and a determination unit that performs a determination regarding the immunochromatographic test piece on the basis of a determination according to a comparison of a measurement value obtained by the measuring unit with a preset threshold value, wherein the measuring unit performs the measurement of the light obtained from the detection portion a plurality of times, and the determination unit performs a determination regarding the immunochromatographic test piece when the determination unit determines that a measurement value in an nth measurement is equal to or greater than the threshold value and also determines that a measurement value in an (n+1)th measurement is equal to or greater than the threshold value.

In this optical measuring device, even when the measurement value in the nth measurement is determined to be equal to or greater than the threshold value, the determination on the immunochromatographic test piece is not immediately performed, and when the measurement value in the subsequent (n+1)th measurement is determined to be equal to or greater than the threshold value, the determination on the immunochromatographic test piece is performed for the first time. By frequently performing such a process during a plurality of measurements, it is possible to rapidly and accurately perform the determination on the immunochromatographic test piece even in a situation in which a state of the detection portion temporally fluctuates.

Further, the detection portion may include a test line and a control line provided on a side behind the test line, and the determination unit may perform the determination on at least one of the test line and the control line. In this case, it is possible to rapidly and accurately perform a determination regarding the immunochromatographic test piece for any of the test line and the control line.

Further, the measuring unit may execute interval measurement in which measurement of light obtained from the test line due to irradiation with the measurement light is performed a plurality of times at predetermined time intervals, and the determination unit may use a positive threshold value for determining a reactivity of an antigen and antibody reaction of the specimen at the test line, and determine that the immunochromatographic test piece is positive when the determination unit determines that a measurement value in an nth interval measurement is equal to or greater than the positive threshold value, and determines that a measurement value in an (n+1)th interval measurement is equal to or greater than the positive threshold value. In this case, it is possible to rapidly and accurately perform the determination that the immunochromatographic test piece is positive.

Further, the measuring unit may execute pre-measurement in which measurement of light obtained from the control line due to irradiation with the measurement light is performed before the interval measurement, and the determination unit may use a pre-coloration threshold value for determining a degree of coloration of the control line in the pre-measurement, and determine that the immunochromatographic test piece is not suitable for measurement when the determination unit determines that a measurement value in an nth pre-measurement is equal to or greater than the pre-coloration threshold value, and determines that a measurement value in an (n+1)th pre-measurement is equal to or greater than the pre-coloration threshold value. The immunochromatographic test piece of which the control line has already been colored to a predetermined intensity or more before the interval measurement is considered to be, for example, a used test piece, that is, a test piece not suitable for measurement. Therefore, by determining the degree of coloration of the control line in the pre-measurement, it is possible to rapidly and accurately perform the determination as to whether the immunochromatographic test piece is not suitable for measurement before the interval measurement.

Further, a plurality of test lines may be provided in the detection portion, and the determination unit may further use a strongly positive threshold value set to a value greater than the positive threshold value, compare a measurement value of another test line in the nth interval measurement with the strongly positive threshold value when the measurement value of one of the test lines in an nth interval measurement is equal to or greater than the positive threshold value and smaller than the strongly positive threshold value, and regard the measurement value of the one test line in the nth interval measurement as being equal to or greater than the positive threshold value when the measurement value of the other test line is smaller than the strongly positive threshold value.

When a measurement value of a certain test line is high enough to exceed the strongly positive threshold value, this may increase the measurement value of another test line. That is, when the certain test line is colored to show strongly positive, this influences a coloration state of the other test line which should originally have been negative, and a measurement result thereof may show positive (referred to as false positive). Therefore, when the measurement value of the one test line is equal to or greater than the positive threshold value and smaller than the strongly positive threshold value, the measurement value of the one test line is regarded as being greater than or equal to the positive threshold value only when the measurement value of the other test line is smaller than the strongly positive threshold value. Thus, degradation in accuracy of the determination due to false positive can be prevented.

Further, the determination unit may further use a positive replacement threshold value set to a value between the positive threshold value and the strongly positive threshold value, compare the measurement value of the one test line in the nth interval measurement with the positive replacement threshold value when the measurement value of the other test line in the nth interval measurement is equal to or greater than the strongly positive threshold value, regard the measurement value of the one test line in the nth interval measurement as being equal to or greater than the positive threshold value when the measurement value of the one test line is equal to or greater than the positive replacement threshold value, and regard the measurement value of the one test line in the nth interval measurement as being smaller than the positive threshold value when the measurement value of the one test line is smaller than the positive replacement threshold value.

In this process, when the measurement value of the other test line in the nth interval measurement is equal to or greater than the strongly positive threshold value, the determination of the one test line is determined by replacing the threshold value with the positive replacement threshold value. Since the positive replacement threshold value is set to a value greater than the positive threshold value, it is possible to perform the determination in consideration of the influence of the coloration of the other test line, and to more reliably prevent degradation in accuracy of the determination due to false positive.

Further, the positive threshold value for use in the first half interval measurement may be set to be greater than the positive threshold value for use in the second half interval measurement. In the first half interval measurement, there is a possibility of a state in which a pigment not related to the test line (a pigment not related to the antigen and antibody reaction related to coloration of the test line) is developing through the test line being measured. Therefore, it is possible to improve accuracy of the determination in the first half interval measurement by setting the positive threshold value for use in the first half interval measurement to be greater than the positive threshold value for use in the second half interval measurement.

Further, the measuring unit may execute specimen development measurement in which light obtained from a portion on the side in front of the test line in the immunochromatographic test piece due to irradiation with the measurement light at any one of times of the interval measurement is measured, and the determination unit may determine whether or not the development of the specimen in the immunochromatographic test piece is abnormal on the basis of a comparison between the measurement value in the specimen development measurement with a preset specimen development measurement threshold value. In this case, it is possible to prevent an erroneous determination caused by an abnormality of the immunochromatographic test piece K itself or an abnormality when dropping the specimen onto this immunochromatographic test piece K.

Advantageous Effects of Invention

According to the optical measuring device according to an aspect of the present invention, it is possible to rapidly and accurately perform a determination regarding the immunochromatographic test piece.

DESCRIPTION OF EMBODIMENTS

Preferred embodiments of an optical measuring device according to an aspect of the present invention will be described in detail below with reference to the drawings.

Figure 1:
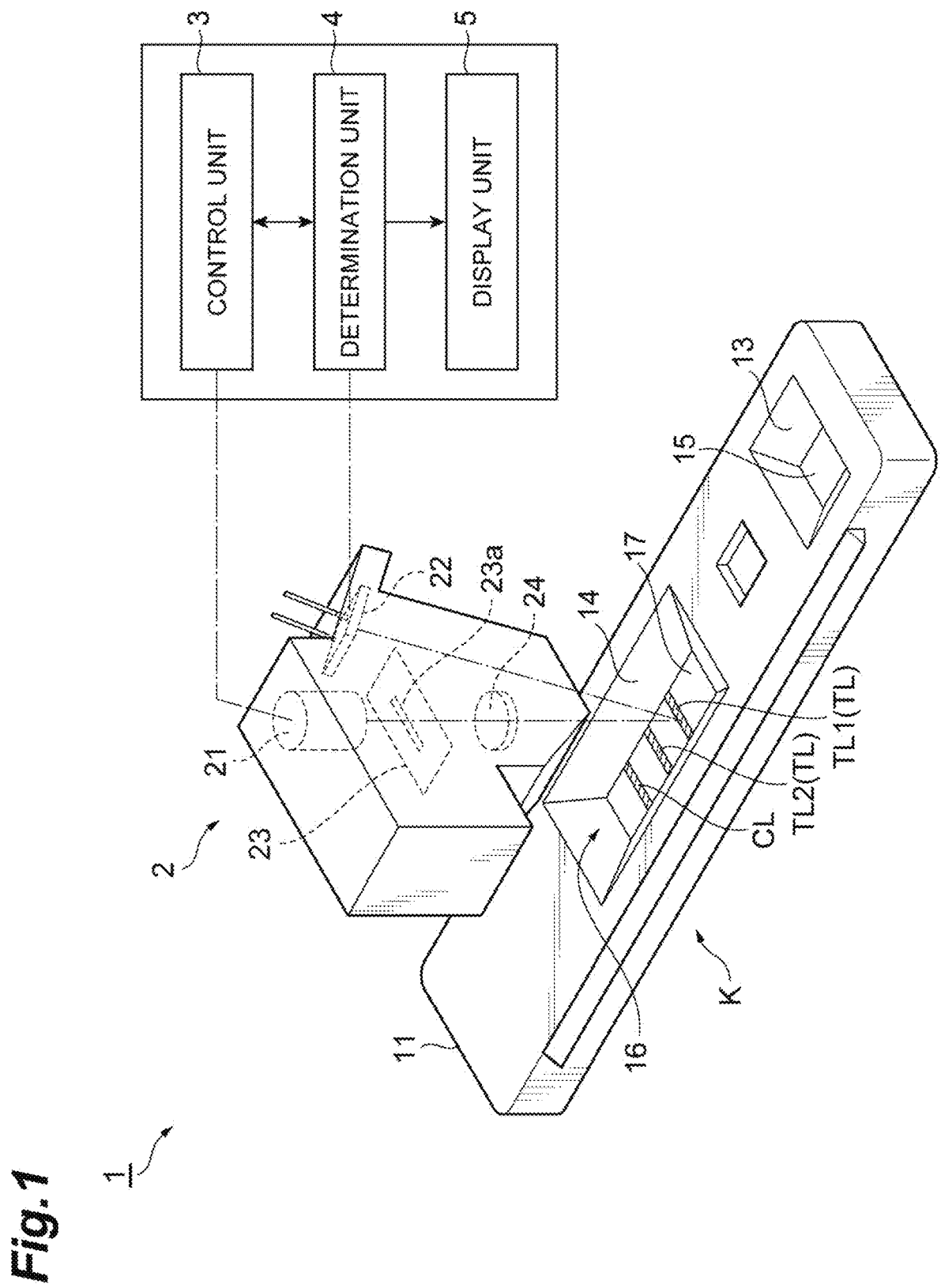
FIG. 1 is a diagram illustrating an embodiment of an optical measuring device.

FIG. 1 is a diagram illustrating an embodiment of an optical measuring device. The optical measuring device 1 illustrated in FIG. 1 is a device that determines a reactivity of an antibody-antigen reaction in a specimen dropped onto an immunochromatographic test piece K by measuring a degree of coloration of a test line TL of the immunochromatographic test piece K.

As illustrated in FIG. 1, the optical measuring device 1 includes an optical head (measuring unit) 2 that performs irradiation of measurement light and measurement of reflected light, a placement plate on which the immunochromatographic test piece K is placed, and a driving mechanism that relatively moves the optical head 2 with respect to the placement plate. Further, the optical measuring device 1 includes, as functional components, a control unit (measuring unit) 3 that controls the optical head 2, a determination unit 4 that performs determination regarding the immunochromatographic test piece K on the basis of a result of measurement of the reflected light, and a display unit 5 that displays a determination result of the determination unit 4. The functional components are realized by, for example, a computer system including a CPU, a storage device such as a RAM and a ROM, an input device such as a keyboard and a mouse, and an auxiliary storage device such as a hard disk.

Figure 2:
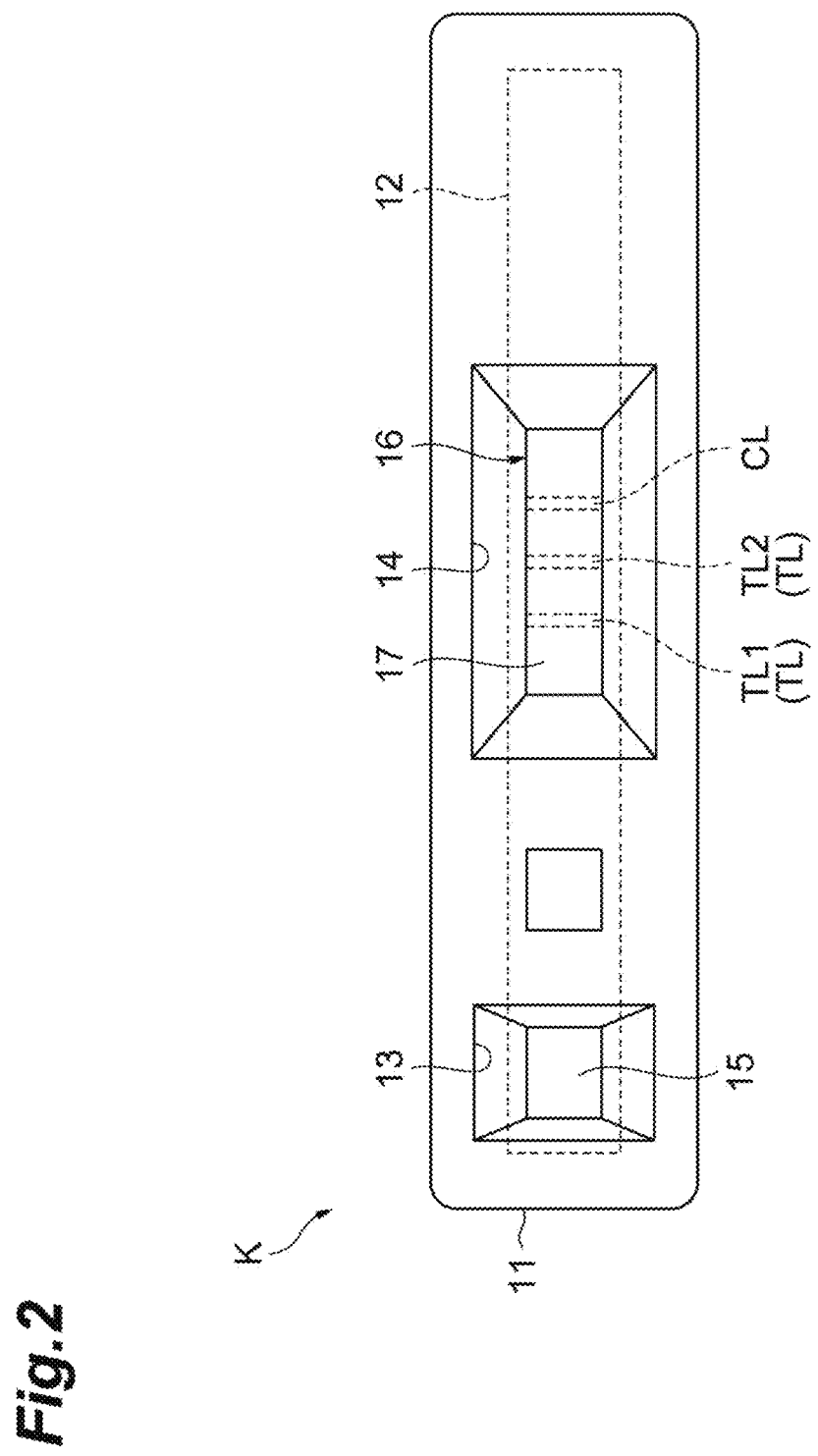
FIG. 2 is a plan view illustrating an example of an immunochromatographic test piece.

As illustrated in FIG. 2, the immunochromatographic test piece K includes a casing 11 having a rectangular shape in a plan view, and a test piece main body 12 held in the casing. A specimen spotting window 13 for dropping a specimen onto one end portion of the test piece main body 12, and an observation window 14 that exposes a substantially central portion of the test piece main body 12 are provided in a longitudinal direction in the casing 11.

The test piece main body 12 is formed in a rectangular shape using, for example, a nitrocellulose membrane or a filter paper. The test piece main body 12 includes a specimen spotting portion 15 provided at a position corresponding to the specimen spotting window 13, and a detection portion 16 provided at a position corresponding to the observation window 14. In the detection portion 16, a test line TL (a first test line TL1 and a second test line TL2) for determining a result of the test and a control line CL for determining whether or not the test has been effectively performed are provided at a constant interval in an order from a front side in a specimen development direction (a direction from the specimen spotting portion 15 to the detection portion 16). Both the test lines TL and the control line CL are provided in a band shape in a direction intersecting the specimen development direction.

The specimen is dropped from the specimen spotting window 13 to the specimen spotting portion 15. The antigen (or antibody) in the specimen binds to a labeling pigment such as a gold colloid labeled antibody (or antigen) contained in the specimen, and develops with time in a longitudinal direction of the test piece main body 12 together with a substance binding to the antigen (or antibody) in the specimen and the labeling pigment, and the unreacted labeling pigment. When the specimen reaches the detection portion 16 with the development of the specimen, the antigen (or antibody) in the specimen specifically reacts with the antibody (or antigen) fixed to the test line TL and the control line CL, and a line-shaped pattern colored with the labeling pigment (coloration line) is formed. The coloration line can be observed through the observation window 14.

The reaction of the reagent progresses over time after the specimen has been dropped onto the immunochromatographic test piece K. The reaction of the reagent usually continues as long as the specimen flowing together with the reagent dries and does not stick to the immunochromatographic test piece K. The degree of coloration of the test line TL varies with time.

As illustrated in FIG. 1, the optical head 2 includes a light emitting element 21, a light detection element 22, a light beam shaping member 23, and a lens 24. In this embodiment, a semiconductor light emitting element such as a light emitting diode (LED) is used as the light emitting element 21, and a semiconductor light detection element such as a silicon (Si) photodiode is used as the light detection element 22. An optical axis of the light emitting element 21 is substantially perpendicular to a surface of the immunochromatographic test piece K, and the measurement light is radiated toward the test piece main body 12. An optical axis of the light detection element 22 is inclined with respect to the optical axis of the light emitting element 21, and an output signal according to an intensity of the reflected light from the test piece main body 12 is output to the determination unit 4.

The light beam shaping member 23 is a plate-like member for shaping the measurement light emitted from the light emitting element 21. A slit 23a extending in the same direction as the test line TL and the control line CL is provided in a central portion of the light beam shaping member 23. The measurement light emitted from the light emitting element 21 passes through the slit 23a, and is shaped to have a light beam cross section in a band shape extending in the same direction as the test line TL and the control line CL. Further, the lens 24 is arranged on an optical axis of the measurement light emitted from the light emitting element 21. The lens 24 focuses the measurement light passing through the light beam shaping member 23 on the test piece main body 12.

The control unit 3 is a unit that performs control of driving of the optical head 2 using the driving mechanism, control of turning on and off the measurement light using the light emitting element 21, processing of an output signal of the light detection element 22, and the like. When the optical head 2 is driven in a longitudinal direction of the immunochromatographic test piece K relative to the placement plate by the control unit 3, the detection portion 16 of the immunochromatographic test piece K is scanned by the measurement light. On the other hand, when the placement plate is driven in the longitudinal direction of the immunochromatographic test piece K with respect to the optical head 2 by the control unit 3, the detection portion 16 of the immunochromatographic test piece K may be scanned by the measurement light. A time required for one scan is sufficiently short with respect to a measurement interval in interval measurement described below and is, for example, about 10 seconds.

The determination unit 4 is a unit that performs a determination regarding the immunochromatographic test piece K from, for example, a reactivity of an antigen and antibody reaction in the specimen. The determination unit 4 calculates a measurement value of reflected light on the basis of the output signal received from the light detection element 22, and determines a reaction status such as whether the immunochromatographic test piece K is positive on the basis of a determination of, for example, the reactivity of the antigen and antibody reaction in the specimen through a comparison of the measurement value with a preset threshold value. The determination unit 4 stores threshold values of three types including a positive threshold value, a strongly positive threshold value, and a positive replacement threshold value, as threshold values for determining the reactivity of the antigen and antibody reaction with respect to the test lines TL. Further, the determination unit 4 stores threshold values of two types including a pre-coloration threshold value and an interval coloration threshold value, as threshold values for determining a degree of coloration for checking the antigen and antibody reaction at the control line TC. These threshold values will be described below. Further, the determination unit 4 outputs information indicating the determination result to the display unit 5, and the display unit 5 displays the determination result on the basis of the information received from the determination unit 4.

Figure 3:
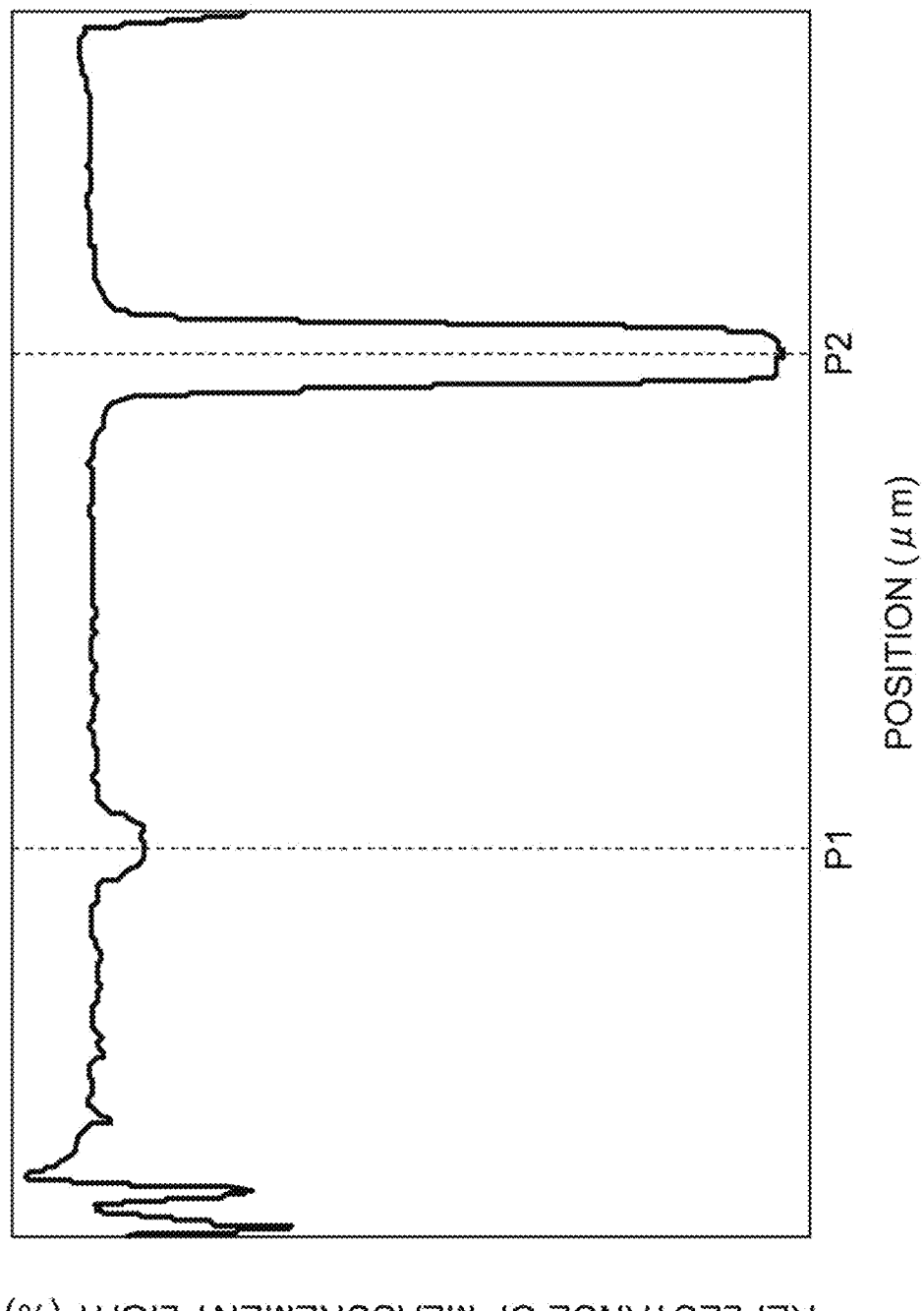
FIG. 3 is a graph illustrating an example of a measurement result of the immunochromatographic test piece obtained in the optical measuring device.

FIG. 3 is a graph illustrating an example of a measurement result of an immunochromatographic test piece obtained by the optical measuring device. The graph illustrated in FIG. 3 shows the degree of coloration of the test lines TI, at a certain time after the specimen has been dropped. A horizontal axis of the graph indicates a position (μm) in the specimen development direction of the detection portion 16 of the immunochromatographic test piece K. Further, a vertical axis of the graph indicates reflected light from each position using reflectance (%).

In this example, a position P1 indicates a position of the first test line TL1, and a position P2 indicates a position of the second test line TL2. When the degree of coloration of the test line TL increases, an absorbance of the measurement light at the test line TL increases. Therefore, the intensity of the reflected light detected by the light detection element 22 decreases according to the degree of coloration of the test line TL. Therefore, by measuring the intensity of the reflected light at the position P1 and the position P2, the degrees of coloration of the first test line TL1 and the second test line TL2 can be detected.

Figure 4:
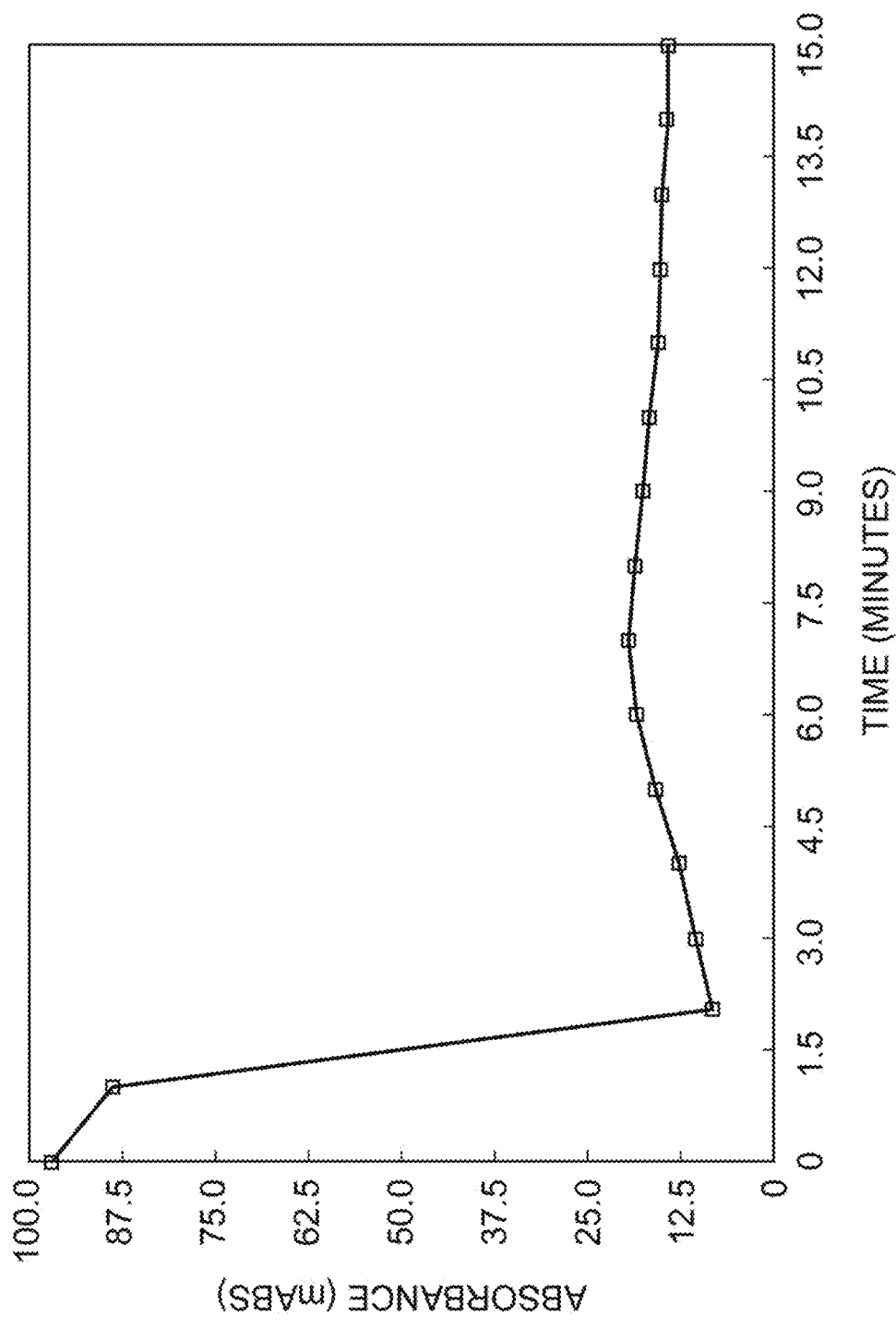
FIG. 4 is a graph illustrating another example of the measurement result of the immunochromatographic test piece obtained in the optical measuring device.

Further, FIG. 4 is a graph illustrating another example of a measurement result of an immunochromatographic test piece obtained by the optical measuring device. The graph illustrated in FIG. 4 shows temporal change in the degree of coloration from dropping of the specimen to reaching of a reaction completion time at the test line TL. A horizontal axis of the graph indicates a time (minutes) after the specimen has been dropped. Further, a vertical axis of the graph indicates the intensity of the reflected light at each time using absorbance (mABS). That is, the graph shows that the higher the absorbance, the higher the degree of coloration of the test line TL.

It can be seen from the graph of FIG. 4 that the degree of coloration of the test line TL temporarily increases due to an influence of a large amount of pigment including a pigment not related to the test line TL (a pigment not related to the antigen and antibody reaction relating to the coloration of the test line TL) developing through the test line TL immediately after the specimen has been dropped. Thereafter, when the pigment not related to the test line TL passes, the degree of coloration of the test line TL converges to a value according to the reactivity of the antigen and antibody reaction in the specimen, accompanied by a slight fluctuation in value.

Subsequently, an operation of the optical measuring device 1 described above will be described in detail.

Figure 5:
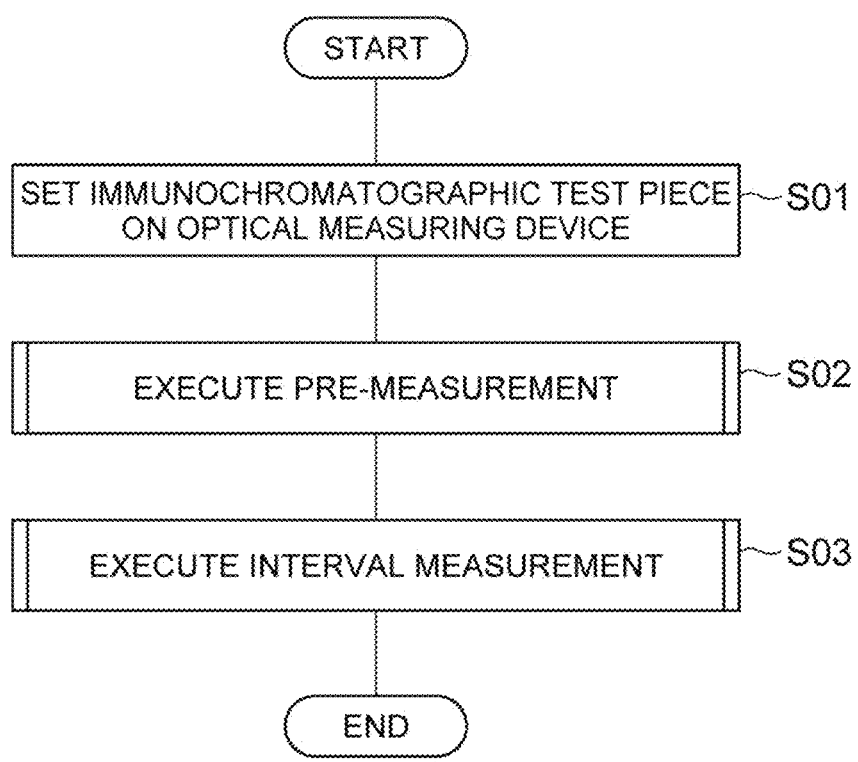
FIG. 5 is a flowchart illustrating an overall operation of the optical measuring device.

FIG. 5 is a flowchart illustrating an overall operation of the optical measuring device. As illustrated in FIG. 5, measurement in the optical measuring device 1 includes pre-measurement and interval measurement. First, an immunochromatographic test piece K is set on the placement plate of the optical measuring device 1 (step S01). The specimen is dropped onto the specimen spotting window 13 of the immunochromatographic test piece K by a measuring person immediately before the specimen is placed on the placement plate, for example. When a start operation (for example, pressing of a start button) is input after the immunochromatographic test piece K is placed on the placement plate, the measurement of the immunochromatographic test piece K is started, and the pre-measurement is executed at the beginning (step S02). In the pre-measurement, in order to confirm the antigen and antibody reaction at the control line CL at an initial stage of the measurement of the immunochromatographic test piece K, it is checked whether or not the immunochromatographic test piece K set on the placement plate is in a state suitable for measurement on the basis of a determination of the degree of coloration of the control line CL through comparison of a measurement value of light obtained from the control line CL with a preset threshold value.

After execution of the pre-measurement, an interval measurement is executed (step S03). The interval measurement is a measurement in which measurement of the light obtained from the test line TL is performed at predetermined time intervals. The interval measurement may be continued until a reaction completion time of the reagent in the immunochromatographic test piece K is reached, or when the determination has been performed before the reaction completion time, the measurement may end at that time. The reaction completion time is set in advance for each immunochromatographic test piece K (a combination of a material of the test piece main body 12 and a type of reagent). For example, when the reaction completion time is ten minutes, the interval measurement is performed up to ten times at intervals of one minute. In this case, the tenth interval measurement is a regular measurement corresponding to the reaction completion time. In each interval measurement, a determination as to whether or not the immunochromatographic test piece K is positive is performed on the basis of a determination of the reactivity of the antigen and antibody reaction in the specimen through a comparison of the measurement value of the light obtained from the test line TL with a preset threshold value.

Figure 6:
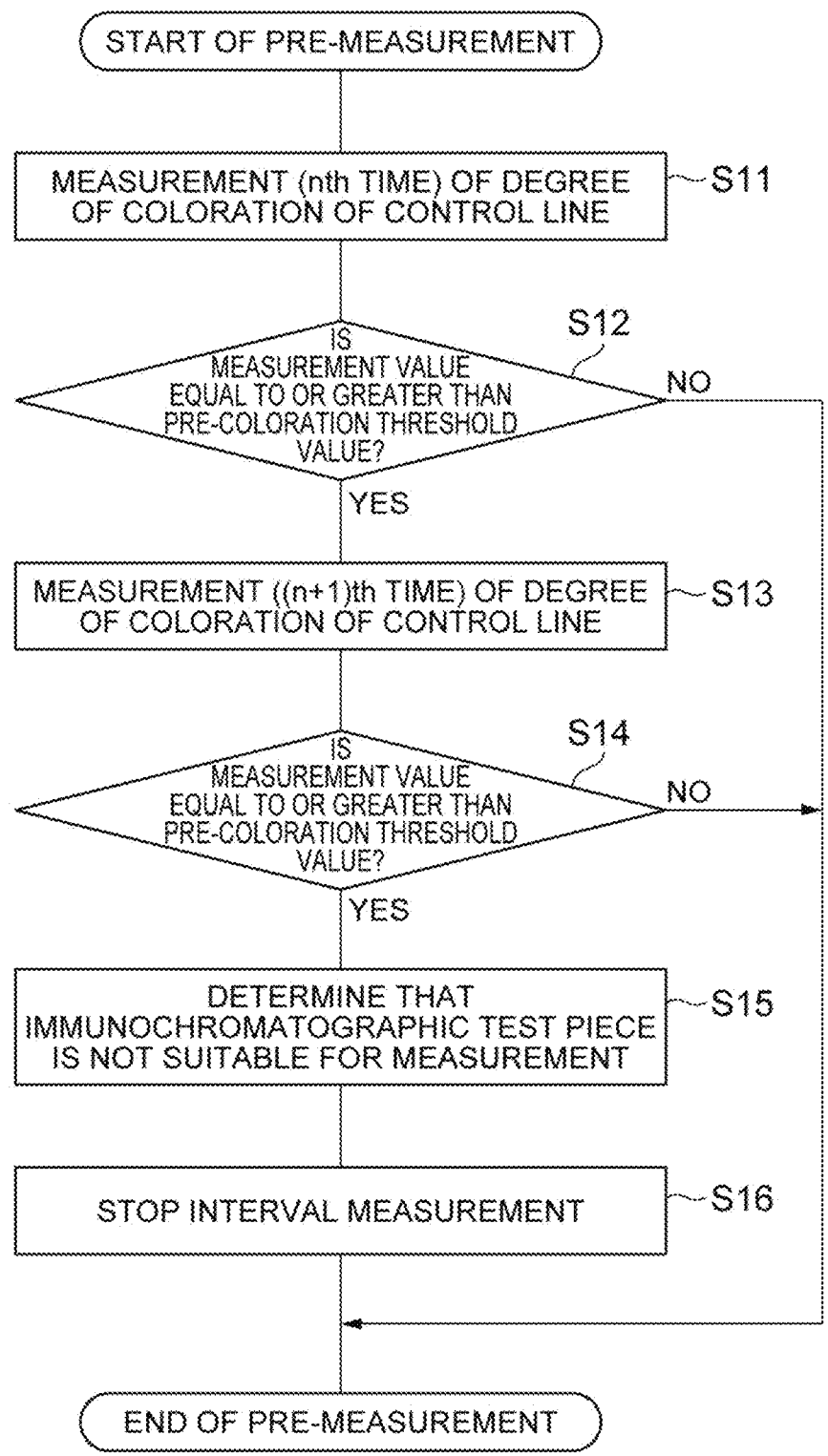
FIG. 6 is a flowchart illustrating an example of pre-measurement.

FIG. 6 is a flowchart illustrating an example of pre-measurement. In the pre-measurement, arbitrary measurement times at an initial stage of the measurement in the optical measuring device 1 can be appropriately selected and used. For example, it is preferable for the first time (n=1) and the second time (n+1=2), the second time (n=2) and the third time (n+1=3), or the like to be selected and used. As illustrated in FIG. 6, in the pre-measurement, the control line CL of the immunochromatographic test piece K is irradiated with the measurement light, and measurement (nth time) of the degree of coloration of the control line CL is performed on the basis of the absorbance of the measurement light (step S11). Then, a determination is performed as to whether or not the measurement value of the control line CL is equal to or greater than a pre-coloration threshold value (step S12). When it is not determined that the measurement value of the control line CL is equal to or greater than the pre-coloration threshold value, that is, when it is determined that the measurement value of the control line CL is smaller than the pre-coloration threshold value, the premeasurement then ends, and transition to the interval measurement occurs.

On the other hand, when it is determined that the measurement value of the control line CL is equal to or greater than the pre-coloration threshold value, the next measurement ((n+1)th time) is performed for the degree of coloration of the control line CL (step S13), and in the (n+1)th time, it is determined whether or not the measurement value of the control line CL is equal to or greater than the pre-coloration threshold value (step S14). When it is determined that the measurement value of the control line CL is smaller than the pre-coloration threshold value in the (n+1)th measurement, the pre-measurement ends and transition to the interval measurement occurs. When it is determined that the measurement value of the control line CL is equal to or greater than the pre-coloration threshold value in the (n+1)th measurement, it is determined that the immunochromatographic test piece K is not suitable for measurement (step S15). In this case, the transition to the interval measurement is stopped and the process is ended (step S16).

The pre-coloration threshold value is a threshold value which is an indicator indicating whether or not the immunochromatographic test piece K to be measured is in a state in which the immunochromatographic test piece K is suitable for measurement. When it is determined that the control line CL has already become colored to a predetermined value or more in a pre-measurement stage at which the specimen should have not yet developed to the control line CL in a state immediately after the specimen has been dropped, that is, in an initial stage of the measurement, it can be determined that the immunochromatographic test piece K is a test piece not suitable for measurement such as a used test piece or a test piece for which too much time has elapsed after the specimen has been dropped. A result of the determination that the immunochromatographic test piece K is not suitable for measurement may be displayed to the measuring person. For example, text, a numerical value, a symbol, or the like indicating the determination result may be displayed on the display unit 5, or may be displayed in various forms such as lighting of a notification light or output of a notification sound.

Figure 7:
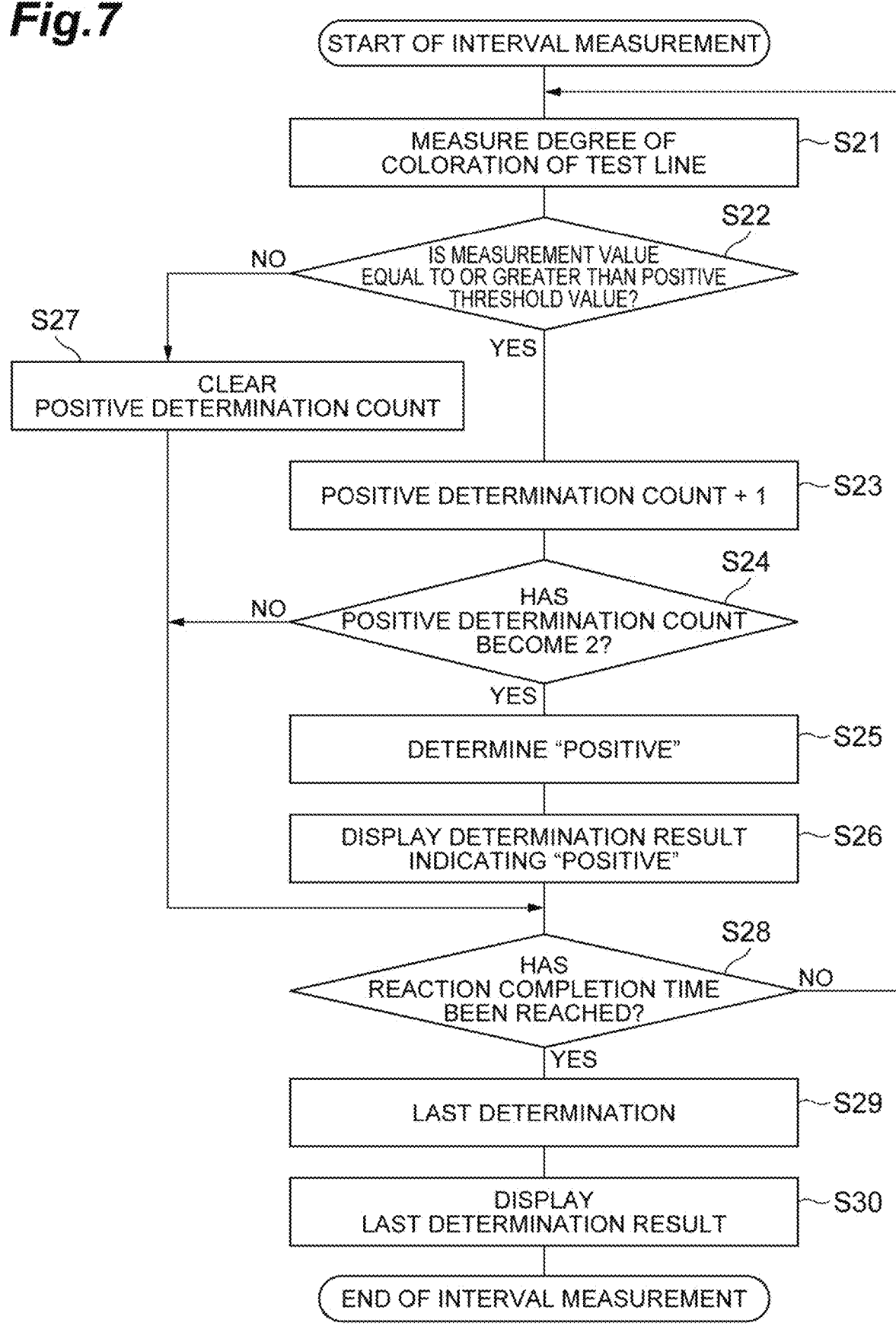
FIG. 7 is a flowchart illustrating an example of interval measurement.

FIG. 7 is a flowchart illustrating an example of the interval measurement. In the flowchart of FIG. 7, processing for one of the first test line TL1 and the second test line TL 2 is shown, but similar processing is executed for the other in parallel. As illustrated in FIG. 7, in the interval measurement, the test line TL of the immunochromatographic test piece K is irradiated with the measurement light, and measurement of the degree of coloration of the test line TL is performed on the basis of the absorbance of the measurement light (step S21). Then, it is determined whether or not the measurement value of the test line TL is equal to or greater than a positive threshold value (step S22).

The positive threshold value is a threshold value which is an indicator indicating whether the antigen and antibody reaction in the specimen is positive or negative. In the embodiment, the positive threshold value for use in the first half of the interval measurement is set to be greater than the positive threshold value for use in the second half of the interval measurement in consideration of temporal change in the degree of coloration of the test line TL as illustrated in FIG. 4. In an example in which the interval measurement is performed ten times at intervals of one minute, for example, the positive threshold value of the first to third times is set to 50 mABS, the positive threshold value of the fourth and fifth times is set to 30 mABS, the positive threshold value of the sixth to ninth times is set to 20 mABS, and the positive threshold value of the tenth time is set to 8 mABS. Thus, when the immunochromatographic test piece is designed, appropriate setting can be performed such that in the first-half interval measurement and the second-half interval measurement, the temporal change in the degree of coloration of the test line TL can be confirmed as illustrated in FIG. 4, and the same applies in the present invention.

When it is determined that the measurement value of the test line TL is equal to or greater than the positive threshold value, one is added to a positive determination count (step S23). An initial value of the positive determination count is 0. After one is added to the positive determination count, it is determined whether or not the positive determination count has become 2 (step S24). When it is determined that the positive determination count becomes two, it is determined that the antigen and antibody reaction in the specimen in the immunochromatographic test piece K is positive (step S25) and the determination result indicating "positive" is displayed on the display unit 5 (step S26).

The determination result indicating "positive" is not limited to text, a numerical value, a symbol, or the like displayed on the display unit 5, and may be displayed in various forms such as lighting of a notification light or output of notification sound. When it is determined in step S22 that the measurement value is smaller than the positive threshold value, the positive determination count is cleared (step S27) and the positive determination count returns to 0, which is the initial value, and then, steps S24 to S26 are skipped. Further, when it is determined in step S24 that the positive determination count has not become 2, steps S25 and S26 are skipped.

Thereafter, it is determined whether or not the reaction completion time has been reached (step S28). When it is determined that the reaction completion time has not been reached, the processes of steps S21 to S27 are repeatedly executed with a predetermined time interval. Further, when it is determined that the reaction completion time has been reached, a last determination is performed (step S29). A last determination result is displayed (step S30), and the interval measurement ends. When it is determined that the antigen and antibody reaction in the specimen is positive in any one of the interval measurements, the determination result indicating "positive" is displayed on the display unit 5, and when it is not determined that the antigen and antibody reaction in the specimen is positive before the interval measurement ends, a determination result indicating "negative" is displayed on the display unit 5.

In the determination unit 4, a determination of the degree of coloration for checking the antigen and antibody reaction at the control line CL in the interval measurement is also performed using an interval coloration threshold value. When it is determined that the measurement value is equal to or greater than the interval coloration threshold value by a predetermined time, it is determined that the development of the specimen has been performed normally. In this case, this fact may be displayed on the display unit 5 or the like, or the interval measurement may be continued without displaying the fact. On the other hand, when it is not determined that the measurement value is equal to or greater than the interval coloration threshold value by the predetermined time, it is determined that there is an abnormality in the development of the specimen. In this case, this fact is displayed on the display unit 5 or the like.

Figure 8:
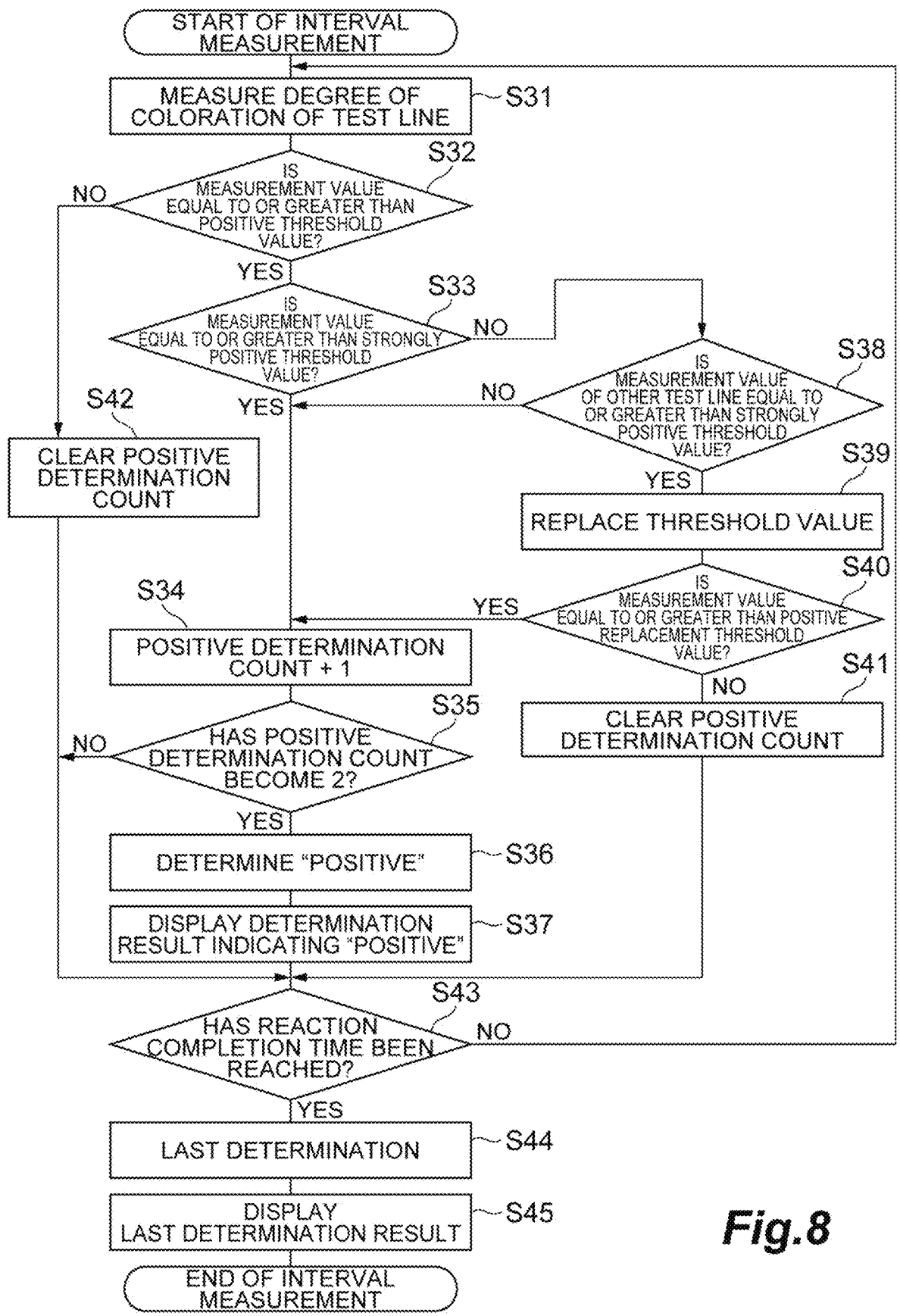
FIG. 8 is a flowchart illustrating another example of the interval measurement.

FIG. 8 is a flowchart illustrating another example of the interval measurement. In the example of the interval measurement illustrated in FIG. 8, the processing related to adding to the positive determination count is different from that in the example of the interval measurement illustrated in FIG. 7.

More specifically, in the interval measurement according to this other example, first, the test line TL of the immunochromatographic test piece K is irradiated with the measurement light, and the measurement of the degree of coloration of the test line TL is performed on the basis of an absorbance of the measurement light (step S31). Then, it is determined whether or not the measurement value of the test line TL is equal to or greater than the positive threshold value (step S32).

In this example, even when the measurement value of the test line TL is equal to or greater than the positive threshold value, adding to the positive determination count is not immediately performed, and it is determined whether or not the measurement value of the test line TL is equal to or greater than the strongly positive threshold value (step S33). The strongly positive threshold value is a threshold value which is an indicator indicating whether the antigen and antibody reaction in the specimen is positive or strongly positive. The strongly positive threshold value is set to a value greater than the positive threshold value. Further, the strongly positive threshold value for use in the first half of the interval measurement may be set to be greater than the strongly positive threshold value for use in the second half of the interval measurement. In an example in which the interval measurement is performed ten times at intervals of one minute, for example, the strongly positive threshold value of the first to third times is set to 250 mABS, the strongly positive threshold value of the fourth and fifth times is set to 200 mABS, the strongly positive threshold value of the sixth to ninth times is set to 150 mABS, and the strongly positive threshold value of the tenth time is set to 100 mABS.

When it is determined that the measurement value of the test line TL is equal to or greater than the strongly positive threshold value, the measurement value of the test line TL is considered to be greater than the positive threshold value since strongly positive is also a type of positive, one is added to the positive determination count, and then, it is determined whether or not the positive determination count has become two (step S34). One is added to the positive determination count, and then, it is determined whether or not the positive determination count has become two (step S35). When it is determined that the positive determination count has become 2, it is determined that the antigen and antibody reaction in the specimen in the immunochromatographic test piece K is positive (step S36) and a determination result indicating "positive" is displayed on the display unit 5 (step S37).

On the other hand, when it is determined in step S33 that the measurement value of the test line TL is smaller than the strongly positive threshold value, it is determined whether or not the measurement value of the other test line TL is equal to or greater than the strongly positive threshold value (step S38). When the measurement value of the other test line TL is smaller than the strongly positive threshold value, the process proceeds to step S34, and one is added to the positive determination count.

When the measurement value of the other test line TL is equal to or greater than the strongly positive threshold value, the positive threshold value is replaced with the positive replacement threshold value (step S39). The positive replacement threshold value is set to a value between the positive threshold value and the strongly positive threshold value. The positive replacement threshold value for use in the first half of the interval measurement may be set to be greater than the positive replacement threshold value for use in the second half of the interval measurement. In an example in which the interval measurement is performed ten times at intervals of one minute, for example, the positive replacement value of the first to third times is set to 60 mABS, the positive replacement threshold value of the fourth and fifth times is set to 40 mABS, the positive replacement threshold value of the sixth to ninth times is set to 30 mABS, and the positive replacement threshold value of the tenth time is set to 20 mABS.

Then, a determination is performed as to whether or not the measurement value of the test line TL is equal to or greater than the positive replacement threshold value (step S40). When it is determined that the measurement value of the test line TL is equal to or greater than the positive replacement threshold value, the measurement value of the test line TL is considered to be equal to or greater than the positive threshold value, the process proceeds to step S34, and one is added to the positive determination count. On the other hand, when it is determined that the measurement value of the test line TL is smaller than the positive replacement threshold value, a determination result in step S32 is considered to be due to false positive, and the positive determination count is cleared (step S41).

In step S32, when it is determined that the measurement value is smaller than the positive threshold value, the positive determination count is cleared (step S42), and steps S33 to S41 are skipped. Further, when it is determined in step S35 that the positive determination count has not become two, steps S36 and S37 are skipped.

Thereafter, it is determined whether or not the reaction completion time has been reached (step S43). When it is determined that the reaction completion time has not been reached, the processes of steps S31 to S42 are repeatedly executed at fixed time intervals. Further, when it is determined that the reaction completion time has been reached, a last determination is performed (step S44). A last determination result is displayed (step S45), and the interval measurement ends.

Figure 9:
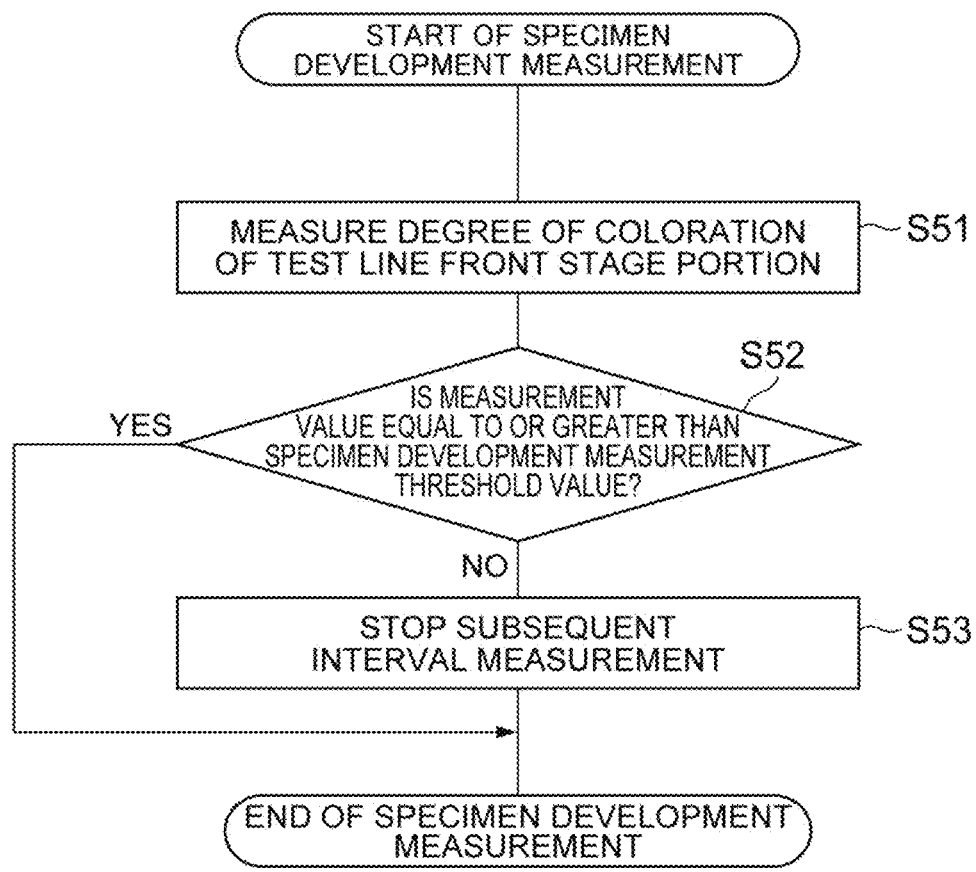
FIG. 9 is a flowchart illustrating an example of specimen development measurement.

Further, during execution of the above-described interval measurement, specimen development measurement is executed to determine a development status of the specimen in the immunochromatographic test piece K after the specimen has been dropped, and determine whether or not the development of the specimen is abnormal. FIG. 9 is a flowchart illustrating an example of the specimen development measurement. This specimen development measurement is executed only once at any one of times of the interval measurement. Further, it is preferable that the specimen development measurement be performed at the time of execution of the initial interval measurement without leaving much time from dropping of the specimen in order to discover an abnormality at an early stage and perform re-testing with another immunochromatographic test piece K.

As illustrated in FIG. 9, in the specimen development measurement, an in front of test line portion 17 of the immunochromatographic test piece K is irradiated with measurement light, and measurement of the degree of coloration of the test line front stage portion 17 is performed on the basis of the absorbance of the measurement light (step S51). The test line front stage portion 17 is a portion on the side in front (the specimen spotting portion 15 side) of the first test line TL1 among portions exposed by the observation window 14 of the detection portion 16 of the test piece main body 12 (see FIG. 2). Then, a determination is performed as to whether or not the measurement value of the test line front stage portion 17 is equal to or greater than a specimen development measurement threshold value (step S52).

When the development of the specimen has been performed normally, the test line front stage portion 17 tends to show a high absorbance since the test line front stage portion 17 is wet with the specimen or the pigment. On the other hand, when the development of the specimen has not been performed normally, the test line front stage portion 17 tends to show a low absorbance since the test line front stage portion 17 is not wet with the specimen. Therefore, when it is determined that the measurement value of the test line front stage portion 17 is equal to or greater than the specimen development measurement threshold value, the development of the reagent in the immunochromatographic test piece K is determined to be normal, and the subsequent interval measurement continues to be executed. On the other hand, when it is determined that the measurement value of the test line front stage portion 17 is smaller than the specimen development measurement threshold value, the development of the specimen in the immunochromatographic test piece K is determined to be abnormal (development failure), and execution of the subsequent interval measurement is stopped (step S53).

As described above, in the optical measuring device 1, even when the measurement value in the nth measurement is determined to be equal to or greater than the threshold value, the determination regarding the immunochromatographic test piece K is not immediately performed, and when the measurement value in the (n+1)th measurement is determined to be equal to or greater than the threshold value, that is, when the measurement value is determined to be equal to or greater than the threshold value consecutively two times, the determination regarding the immunochromatographic test piece K is performed for the first time. In the optical measuring device 1, for example, it is determined whether or not the immunochromatographic test piece K is positive by performing determination on the test line TL in the interval measurement, and it is determined whether or not the immunochromatographic test piece K is inappropriate for measurement by performing determination on the control line CL in the advance measurement.

By performing such a process, even in a situation in which the degree of coloration of the test line TL temporally fluctuates, it is possible to accurately perform the determination as to whether or not the immunochromatographic test piece K is positive, for example, as illustrated in FIG. 4. Further, even when an erroneous determination is temporarily performed in an n-th measurement due to noise or the like at the time of measurement, since the re-determination is performed in the (n+1)th measurement, an erroneous final determination due to a temporary error of the device or the measurement can be prevented and a high-accuracy determination can be performed. Further, it is possible to perform the determination as to whether or not the immunochromatographic test piece K is positive, at any time during the interval measurement.

Further, in the optical measuring device 1, when the measurement value of one test line TL in the nth interval measurement is equal to or greater than the positive threshold value and smaller than the strongly positive value threshold value, the measurement value of the other test line TL in the nth interval measurement is compared with the strongly positive threshold value. When the measurement value of the other test line TL is smaller than the strongly positive threshold value, the measurement value of the one test line TL in the nth interval measurement is regarded as being equal to or greater than the positive threshold value, and addition to the positive determination count is performed.

When a measurement value of a certain test line is high enough to exceed the strongly positive threshold value, this may increase the measurement value of another test line. That is, when a certain test line is colored to show strongly positive, this influences a coloration state of the other test line which should originally have been negative, and a measurement result thereof may show positive. Therefore, when the measurement value of the one test line TL is equal to or greater than the positive threshold value and smaller than the strongly positive threshold value, the measurement value of the one test line TL is regarded as being greater than or equal to the positive threshold value only when the measurement value of the other test line TL is smaller than the strongly positive threshold value. Thus, degradation in accuracy of the determination due to false positive can be prevented.

Further, in the optical measuring device 1, when the measurement value of the other test line TL in the nth interval measurement is equal to or greater than the strongly positive threshold value, the positive threshold value is replaced with the positive replacement threshold value, and the measurement value of the one test line TL is compared with the positive replacement threshold value. When the measurement value of the one test line TL is equal to or greater than the positive replacement threshold value, the measurement value of the one test line TL in the nth interval measurement is regarded as being equal to or greater than the positive threshold value, and addition to the positive determination count is performed. Further, when the measurement value of the one test line TL is smaller than the positive replacement threshold value, the measurement value of the one test line TL in the nth interval measurement is regarded as being smaller than the positive threshold value, and the addition to the positive determination count is suspended.

According to this process, since the positive replacement threshold value is set to a value greater than the positive threshold value, it is possible to perform the determination in consideration of the influence of the coloration on another test line TL. Therefore, it is possible to more reliably prevent degradation in accuracy of the determination due to false positives.

Further, in the optical measuring device 1, the positive threshold value for use in a first half interval measurement is set to be greater than the positive threshold value for use in a second half interval measurement. In the first half interval measurement, there is a possibility of a state in which a pigment not related to the test line TL (a pigment not related to the antigen and antibody reaction related to coloration of the test line TL) is developing through the test line TL being measured (see FIG. 4). Therefore, it is possible to improve accuracy of the determination in the first half interval measurement by setting the positive threshold value for use in the first half interval measurement to be greater than the positive threshold value for use in the second half interval measurement.

Further, the optical measuring device 1 performs pre-measurement of measuring the light obtained from the control line CL due to irradiation with the measurement light before starting the interval measurement. The optical measuring device 1 determines whether or not the control line CL is colored on the basis of a measurement value in the pre-measurement, and stops execution of the interval measurement when the optical measuring device 1 determines that the control line CL is colored. The immunochromatographic test piece K in which the control line CL has been already colored is considered to be a test piece not suitable for measurement, for example, a used test piece. Therefore, by performing the pre-measurement of the control line CL, it is possible to rapidly and accurately determine whether the immunochromatographic test piece K is not suitable for measurement before start of the interval measurement.

Further, the optical measuring device 1 executes the specimen development measurement to measure light obtained from the test line front stage portion 17 due to the irradiation with the measurement light at any one of the times of interval measurement. The optical measuring device determines whether or not the development of the specimen in the immunochromatographic test piece K is abnormal on the basis of a comparison between the measurement value obtained in the specimen development measurement and a preset development measurement threshold value, and may determine that the development of the specimen is abnormal. Further, when it is determined that the development of the specimen is abnormal, execution of the subsequent interval measurement may be stopped. By executing such a process, it is possible to prevent an erroneous determination caused by an abnormality of the immunochromatographic test piece K itself or an abnormality when dropping a specimen onto this immunochromatographic test piece K.

The present invention is not limited to the above embodiment. For example, in the above embodiment, when it is determined that the immunochromatographic test piece K is positive in the interval measurement before the reaction completion time, a display of "positive" on the display unit 5 is performed and the subsequent interval measurement is performed. However, when it is determined that the immunochromatographic test piece K is positive in the interval measurement before the reaction completion time, this may be regarded as a last determination result, and the process may be ended without waiting for the reaction completion time to be reached. Further, the specimen development measurement illustrated in FIG. 9 is not necessarily performed. The optical measuring device 1 may be configured to be capable of receiving an input of an instruction regarding execution or non-execution of the specimen development measurement.

In the above embodiment, the immunochromatographic test piece K in which the two test lines TL (the first test line TL1 and the second test line TL2) are provided is exemplified, but the present invention is also applicable to an immunochromatographic test piece in which only one test line TL is provided or an immunochromatographic test piece in which three or more test lines TL are provided. In a case where the present invention is applied to an immunochromatographic test piece in which the three or more test lines TL are provided, when it is determined whether or not a measurement value of the other test line TL is equal to or greater than the strongly positive threshold value (see step S38 in FIG. 8), the determination may be performed on the other adjacent test lines TL, for example.

Further, according to a viscosity of a sample containing the immunochromatographic test piece K or the specimen, a measurement value at the first interval measurement is not necessarily highest. For example, the positive threshold value for use in the first interval measurement among the positive threshold values for use in the first half interval measurement may not be set to be highest, and the positive threshold value for use in an interval measurement after the first interval measurement may be set to be highest.

REFERENCE SIGNS LIST

1 Optical measuring device
2 Optical head (measuring unit)
3 Control unit (measuring unit)
4 Determination unit
16 Detection portion
K Immunochromatographic test piece
TL Test line
CL Control line

The invention claimed is:

1. An optical measuring device comprising:
a measuring unit configured to irradiate a detection portion of an immunochromatographic test piece with measurement light and measure light obtained from the detection portion due to the irradiation with the measurement light; and
a determination unit configured to perform a determination regarding the immunochromatographic test piece on the basis of a determination according to a comparison of a measurement value obtained by the measuring unit with a preset threshold value,
wherein the measuring unit is configured to perform the measurement of the light obtained from the detection portion a plurality of times, and
the determination unit is configured to not immediately perform a determination regarding the immunochromatographic test piece when a measurement value in an nth measurement is equal to or greater than the threshold value and perform the determination regarding the immunochromatographic test piece when the determination unit determines that a measurement value in an (n+1)th measurement is equal to or greater than the threshold value consecutively following the nth measurement.

2. The optical measuring device according to claim 1, wherein the detection portion includes a test line and a control line provided on a side behind the test line, and the determination unit performs the determination on at least one of the test line and the control line.

3. The optical measuring device according to claim 2, wherein the measuring unit executes interval measurement in which measurement of light obtained from the test line due to irradiation with the measurement light is performed a plurality of times at predetermined time intervals, and
the determination unit uses a positive threshold value for determining a reactivity of an antigen and antibody reaction of a specimen at the test line, and determines that the immunochromatographic test piece is positive when the determination unit determines that a measurement value in an nth interval measurement is equal to or greater than the positive threshold value, and determines that a measurement value in an (n+1)th interval measurement is equal to or greater than the positive threshold value.

4. The optical measuring device according to claim 3, wherein the measuring unit executes pre-measurement in which measurement of light obtained from the control line due to irradiation with the measurement light is performed before the interval measurement, and
the determination unit uses a pre-coloration threshold value for determining a degree of coloration of the control line in the pre-measurement, and determines that the immunochromatographic test piece is not suitable for measurement when the determination unit determines that a measurement value in an nth pre-measurement is equal to or greater than the pre-coloration threshold value, and determines that a measurement value in an (n+1)th pre-measurement is equal to or greater than the pre-coloration threshold value.

5. The optical measuring device according to claim 3,
wherein a plurality of test lines are provided in the detection portion, and
the determination unit further uses a strongly positive threshold value set to a value greater than the positive threshold value, compares a measurement value of another test line in the nth interval measurement with the strongly positive threshold value when the measurement value of one of the test lines in the nth interval measurement is equal to or greater than the positive threshold value and smaller than the strongly positive threshold value, and regards the measurement value of the one test line in the nth interval measurement as being equal to or greater than the positive threshold value when the measurement value of the other test line is smaller than the strongly positive threshold value.

6. The optical measuring device according to claim 5,
wherein the determination unit further uses a positive replacement threshold value set to a value between the positive threshold value and the strongly positive threshold value, compares the measurement value of the one test line in the nth interval measurement with the positive replacement threshold value when the measurement value of the other test line in the nth interval measurement is equal to or greater than the strongly positive threshold value, regards the measurement value of the one test line in the nth interval measurement as being equal to or greater than the positive threshold value when the measurement value of the one test line is equal to or greater than the positive replacement threshold value, and regards the measurement value of the one test line in the nth interval measurement as being smaller than the positive threshold value when the measurement value of the one test line is smaller than the positive replacement threshold value.

7. The optical measuring device according to claim 3,
wherein the positive threshold value for use in a first half interval measurement is set to be greater than the positive threshold value for use in a second half interval measurement.

8. The optical measuring device according to claim 3,
wherein the measuring unit executes specimen development measurement in which light obtained from a portion on the front stage side relative to the test line in the immunochromatographic test piece due to irradiation with the measurement light at any one of times of the interval measurement is measured, and
the determination unit determines whether or not the development of the specimen in the immunochromatographic test piece is abnormal on the basis of a comparison between the measurement value in the specimen development measurement with a preset specimen development measurement threshold value.

* * * * *